(12) United States Patent
Dufour et al.

(10) Patent No.: US 8,974,802 B2
(45) Date of Patent: Mar. 10, 2015

(54) MEDICAMENT FOR THE TREATMENT OF CANCER OF THE PANCREAS

(75) Inventors: Emmanuelle-Cécile Dufour, Lyons (FR); Yann Godfrin, Lyons (FR)

(73) Assignee: Erytech Pharma, Lyons (FR)

( * ) Notice: Subject to any disclaimer, the term of this patent is extended or adjusted under 35 U.S.C. 154(b) by 292 days.

(21) Appl. No.: 12/810,164

(22) PCT Filed: Dec. 24, 2008

(86) PCT No.: PCT/EP2008/068289
§ 371 (c)(1),
(2), (4) Date: Jul. 29, 2010

(87) PCT Pub. No.: WO2009/080837
PCT Pub. Date: Jul. 2, 2009

(65) Prior Publication Data
US 2010/0310612 A1    Dec. 9, 2010

(30) Foreign Application Priority Data

Dec. 24, 2007   (FR) ...................................... 07 60345

(51) Int. Cl.
| | |
|---|---|
| A61K 9/50 | (2006.01) |
| A61K 38/48 | (2006.01) |
| A61P 35/00 | (2006.01) |
| A61K 38/50 | (2006.01) |
| A61K 9/00 | (2006.01) |
| A61K 9/10 | (2006.01) |
| A61K 31/282 | (2006.01) |

(52) U.S. Cl.
CPC .............. *A61K 38/50* (2013.01); *A61K 9/0019* (2013.01); *A61K 9/10* (2013.01); *A61K 9/5068* (2013.01); *A61K 31/282* (2013.01)
USPC ........................................ 424/400; 424/94.63

(58) Field of Classification Search
None
See application file for complete search history.

(56) References Cited

U.S. PATENT DOCUMENTS

| | | | |
|---|---|---|---|
| 7,985,548 B2 | 7/2011 | Lorenzi et al. | |
| 2008/0261262 A1* | 10/2008 | Godfrin | 435/30 |

FOREIGN PATENT DOCUMENTS

| | | | | |
|---|---|---|---|---|
| FR | 2873925 | * | 2/2006 | C12M 1/33 |

OTHER PUBLICATIONS

Ducreux, M. et al. Annals of Oncology, 2004, vol. 15, pp. 467-473.*
Yunis, A. A. et al. International Journal of Cancer, 1977, vol. 19, pp. 128-135.*
Zocchi, E. et al. Proceedings of the National Academy of Sciences (USA), 1989, v. 86, pp. 2040-2044.*
Palmer, K. R. et al. British Journal of Surgery, 1994, v. 81, pp. 882-885.*
Poznansky, M. J.; Shandling, M.; Salkie, M. A. "Advantages in the use of L-asparaginase-Albumin Polymer as an antitumor agent." Cancer Research, 1982, 42, 1020-1025.*

(Continued)

*Primary Examiner* — Mina Haghighatian
*Assistant Examiner* — Erin Hirt
(74) *Attorney, Agent, or Firm* — B. Aaron Schulman, Esq.; Stites & Harbison, PLLC

(57) ABSTRACT

The invention relates to a suspension of red corpuscles encapsulating asparaginase as a medicament for treating pancreatic cancer. It in particular concerns a therapeutic composition or medicament intended for the treatment of pancreatic cancer, containing an effective quantity of such a suspension of red corpuscles.

12 Claims, 3 Drawing Sheets

(56) References Cited

OTHER PUBLICATIONS

International Search Report for PCT/EP2008/068289.
Millan C G et al: "Drug, enzyme and peptide delivery using erythrocytes as carriers" Journal of Controlled Release, Elsevier, Amsterdam, NL, vol. 95, No. 1, (Feb. 20, 2004), pp. 27-49.
Kravtzoff R et al:"Erythrocytes as Carriers for L-Asparaginase Methodological and Mouse In-Vivo Studies", Journal of Pharmacy and Pharmacology, London, GB, vol. 42, No. 7, (Jul. 1, 1990), pp. 473-476.
Lessner H E et al: "Phase 2 Study of L Asparaginase in the Treatment of Pancreatic Carcinoma" Cancer Treatment Reports, vol. 64, No. 12, 1980, pp. 1359-1361.
Lessner H E et al: "Treatment of Pancreatic Carcinoma With L Asparaginase" Digestion, vol. 16, No. 3, 1977, p. 255.
Burris et al: "Assessing clinical benefit in the treatment of pancreas cancer: Gemcitabine compared to 5-fluorouracil" European Journal of Cancer, Pergamon Press, Oxford, GB, vol. 33, (Jan. 1, 1997), pp. S18-S22.
Fan Zhao et al: "Gemcitabine and oxaliplatin combination chemotherapy in 30 patients with advanced pancreatic carcinoma" The Chinese-German Journal of Clinical Oncology, Springer-Verlag, BE, vol. 6, No. 5, (Oct. 1, 2007), pp. 461-463.
Knoderer et al, "Predicting Asparaginase-Associated Pancreatitis", 2007, vol. 49, pp. 634-639, Pediatr. Blood Cancer.
Mathe, et al, "The Place of the L-Asparaginase in the Treatment of Acute Leukemias", 1970, vol. 33, pp. 279-287, Recent Results Cancer Res.
Woo et al, "Hypersensitivity or Development of Antibodies to Asparaginase Does Not Impact Treatment Outcome of Childhood Acute Lymphoblastic Leukemia", Apr. 2000, vol. 18, No. 7, pp. 1525-1532, Journal of clinical Oncology.
Zubrod, et al, "The Clinical Toxicities of L-Asparaginase in Treatment of Leukemia and Lymphoma", vol. 45, No. 4, pp. 555-559, Pediatrics.
Wu, et al, "Sensitivity of Cultured Pancreatic Carcinoma Cells to Acinetobacter Glutaminase-Asparaginase", Sep. 1982, vo. 18, No. 9, pp. 750-754, In Vitro.
Gong W, et al., "Advances in the application of erythrocytes as drug carriers", 2006, pp. 1312-1350, The $6^{th}$ Acad. Annual Meeting of the Pharm. Soc. of China.
Woo, et al, "Anti-asparaginase antibodies following E. coli asparaginase therapy in pediatric acute lymphoblastic leukemia", 1998, pp. 1527-1533, Leukemia.
Wang, et al, "Evaluation of immunologic crossreaction of antiasparaginase antibodies in acute lymphoblastic leukemia (ALL) and lymphoma patients", 2003, pp. 1583-1588, vol. 17, Leukemia.
Yunis, et al, "Human Pancreatic Carcinoma (MIA PaCa-2) in Continuous Culture: Sensitivity to Asparaginase", 1977, pp. 128-135, vol. 19, Int. J. Cancer.
Wu, et al, "Mechanism of Sensitivity of Cultured Pancreatic Carcinoma to Asparaginase", 1978, pp. 728-733, vol. 22, Int. J. Cancer.
Sapra, et al, "In vitro and in vivo evaluation of pegaspargase (Oncaspar®) for the treatment of solid tumors and lymphomas", 2006, AACR.
Denis, et al, "Preclinical evaluation of PEG-L-asparaginase for pancreatic cancer", 1999, vol. 23, Proc. Am. Assoc. Cancer Res.
Orsonneau, et al, "Dosage automatique en cinetique de l'activite L-asparaginase plasmatique en suivi therapeutique des leucemies aigues lymphobiastiques", Sep.-Oct. 2004, pp. 568-572, vol. 62, No. 5, Annalas da Biologie Clinique.
Muller, et al, "Use of L-asparaginase in childhook ALL", 1998, pp. 97-113, vol. 28, Hematology.
Kravtzoff, et al, "Tolerance Evaluation of L-asparaginase loaded in red blood cells", 1996, pp. 221-225, vol. 51, Eur. J. Clin. Pharmacol.

\* cited by examiner

Figure 1: First calculation method of the half-life
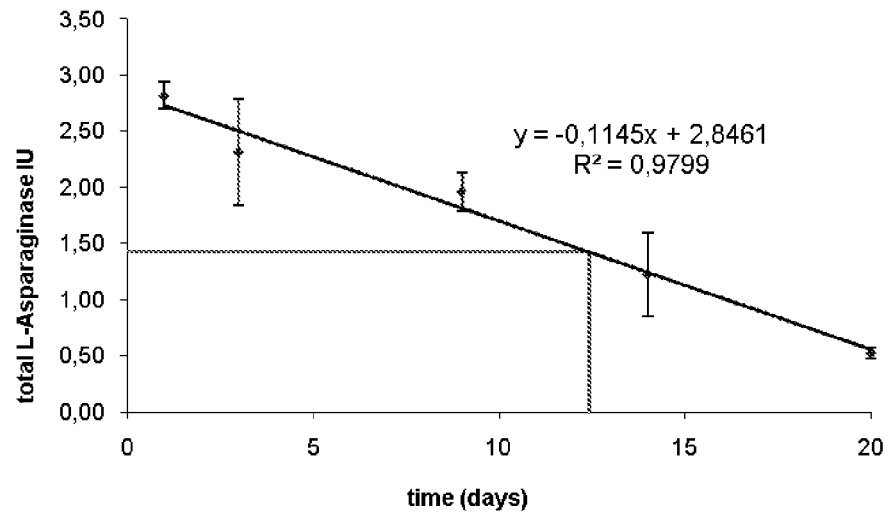
Figure 2: Second calculation method of the half-life
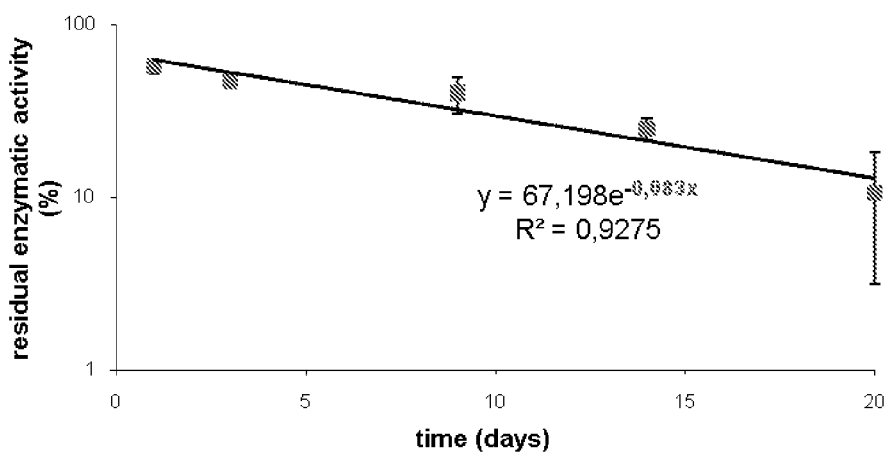

MEDICAMENT FOR THE TREATMENT OF CANCER OF THE PANCREAS

The present invention relates to the therapeutic treatment of pancreatic cancer. It concerns in particular a novel composition for the treatment of this cancer and an associated therapeutic treatment method.

Cancer of the pancreas is the sixth most common cause of death due to cancer in France (7181 deaths in 2000), and the fifth most common cause of death due to cancer in the industrialized countries, and in the United States it has become the fourth most common cause of death in man. In France its incidence is from 5 to 10/100,000 inhabitants per year and is increasing slightly (1 to 2%) every year. It represents 7% of the cancers of the digestive system and affects men (60%) more often than women (40%). Since the diagnosis is often made at the advanced stage, metastases are detected in half of the cases, with the result that the average survival time in this cancer is only a few months with 4 to 6% of survivors at 5 years. The survival median, all stages combined, is from 4 to 7 months and it increases by 15 to 18 months in patients who have undergone resection.

If the tumour is not operable or exhibits metastases, chemotherapy may be considered in informed patients in good general condition. The response rates are of the order of 15 to 30%. The medicaments used are gemcitabine (Burris et al., European Journal of Cancer, 1997, 33:18-22), the combination gemcitabine and oxaliplatin (Zhao et al., Chinese-German Journal of Clinical Oncology, 2007, 6(5):461-463), and 5-fluorouracil in combination with a platinum derivative. These chemotherapies make it possible to moderately increase the survival median of patients with metastases, which is 4 to 6 months without treatment.

In spite of the progress recorded with novel chemotherapies, the prognosis for cancer of the pancreas remains very poor. Even in patients operated for curative purposes, the survival rate is only about 20% at 5 years, owing to local and metastatic relapses.

In the face of the severity and very poor prognosis associated with cancer of the pancreas, and the progressive increase in its incidence in the population of Western countries in particular, there is a real need to propose an alternative treatment more effective than those currently proposed.

Asparaginase is an enzyme produced from bacterial microorganisms (*E. coli* or *Erwinia chrysanthemi*) which has been used for about thirty years in anti-leukaemia chemotherapy. This enzyme hydrolyses and depletes asparagine, an amino acid essential for the production of the proteins necessary for cell life. Now, in contrast to normal cells, certain cancerous lymphoblastic cells do not have the capacity to produce their asparagine themselves and are dependent on extra-cellular sources for the synthesis of their proteins. Treatment with asparaginase deprives them of this essential constituent and thus leads to their death. This antimitotic agent is selective for tumour cells.

However, natural asparaginase induces the production of circulating antibodies causing an increase in the clearance of asparaginase, and allergic reactions, sometimes very severe (Wang B et al., Leukemia, 2003; (8): 1583-1588). Moreover, the short half-life of the enzyme (24 hrs) necessitates repeated injections and hospitalizations. These major limitations led to the development of a pegylated form, PEG-asparaginase, which has been approved by the FDA for first-line treatment of acute lymphoblastic leukaemia (LAL).

In the 1980s, various authors studied the effects of in vitro asparaginase on human pancreatic cancer cell lines.

The first evidence of an effect of asparaginase on a human pancreatic cancer cell line (MIA Paca-2) was described in 1977 par Yunis et al. (Yunis A A et al., Int J Cancer, 1977; 19(1): 128-35). Asparaginase, incubated in the presence of MIA Paca2 cells has a significant effect on the growth of the cells at a concentration of 0.1 IU/ml with total inhibition of cell growth with cell death at concentrations of 0.5 and 1 IU/ml.

The authors also show that this effect is specific to pancreatic cells since asparaginase (used at a concentration of 1 IU/ml) has an effect on another cancerous pancreatic line (PANC-1). But no effect of asparaginase on the growth of human pulmonary and melanoma cells is observed. The authors did not determine the mechanism of the sensitivity of the MIA Paca-2 cells to asparaginase.

The following year, the studies of Wu et al. confirmed these results on MIA Paca-2 and PANC-1 cells (Wu M. et al., Int J Cancer, 1978 22(6):728-33). Although the mechanism is still not clear, these authors suggested that the action of asparaginase on cancerous pancreatic cells takes place via inhibition of protein synthesis.

These results were also obtained with another enzyme, *Acinetobacter* Glutaminase Asparaginase (AGA), with better efficacy than asparaginase (WU M C et al., In Vitro, 1982 September; 18(9): 750-4). The authors show that this enzyme totally inhibits the cell growth of MIA Paca-2 and PANC-1 cells at a concentration of 0.0025 IU/ml (no effect at this concentration with asparaginase) and that this activity also takes place via the glutaminase activity of the enzyme.

In 1977 Lessner et coll. (Lessner H E, et al., Digestion, 1977, 16(3):255) announced a clinical trial to delineate a possible role for L-Asp in the treatment of pancreatic carcinoma, however they already shown no response for Two of the patients and side-effects. Interest in using asparaginase in the treatment of cancer of the pancreas came to an abrupt halt following the publication of results obtained during the phase II clinical trial intended to test the efficacy of asparaginase in the treatment of pancreatic carcinoma (Lessner H E, et al. Cancer Treat. Rep., 1980; 64:1359-1361). *E. coli* asparaginase was injected IV at 1000 IU/kg/day into ten patients suffering from inoperable pancreatic cancer. Serious side-effects appeared rapidly. The treatment was therefore stopped early. Thus the only clinical trial performed concluded that asparaginase had no therapeutic interest in the case of pancreatic cancer.

More recently, a recovery of interest has been seen with studies relating to pegylated forms of asparaginase.

In a preclinical study presented at the AACR Congress in 1999 (Denis L J et al. Proc Am Assoc Cancer Res, 1999: p. 23) the addition of PEG-asparaginase at 1 IU/ml made it possible to inhibit cell growth by 61% (MIA Paca-2), 100% (PANC-1) and 51% for BxPC-3 cells incubated in the presence of 10 IU/ml PEG-asparaginase. The $IC_{50}$ of PEG-asparaginase for MIA Paca-2 and PANC-1 cells is 0.13 and 0.25 IU/ml respectively. The authors also performed an experiment in vivo by implanting MIA Paca-2 cells into nude mice. After treatment of these mice by injection of PEG-asparaginase (12.5 IU/g or 25 IU/g per day i/p) for 14 days with or without gemcitabine (80 mg/kg i/p on days 1, 4, 7 and 10), the authors observe cell growth inhibition of 59% (PEG-asparaginase alone), 63.5% (gemcitabine alone) and 85.9% (PEG-asparaginase and gemcitabine).

Complementary results were presented at the 2006 AACR Congress (Supra P. et al. AACR November 2006). This study presents the in vitro and in vivo evaluation of PEG-asparaginase (Oncaspar®, Enzon Pharmaceuticals) for the treatment of solid tumours (pancreas, ovary and lymphoma). The in vitro cytotoxicity of PEG-asparaginase ($IC_{50}$) is 0.27 IU/ml (PANC-1), 0.66 IU/ml (MIA Paca-2), 0.46 IU/ml (PANC 10.05), and greater than 20 IU/ml (CFPAC-2 and AsPC-1). The in vivo efficacy of PEG-asparaginase was determined on xenografts of MIA Paca-2 cells ($2.5 \times 10^6$ cells) implanted into mice. Thus one treatment with PEG-asparaginase (0.8 kIU/kg) makes it possible to decrease the tumour volume by 14%, gemcitabine (80 mg/kg) enables a decrease of 29% and the combination of the two enables a decrease of 48%. The combination of PEG-asparaginase (Oncaspar®) and gemcitabine (Gemzar®) has an inhibitory effect on the growth of solid tumours.

As asparaginase has been used for more than 30 years, the undesirable effects associated with this enzyme are well known, the main ones being certain allergies with clinical symptoms, diabetes and pancreatitis, mental disorders and coagulation disorders.

The administration of asparaginase causes hyper-sensitivity reactions in man. The mechanism of onset is complex and at the present time has not been completely elucidated. Asparaginase is a direct immunogen owing to its high molecular weight (>100,000 Da) and its protein nature. The hypersensitivity reactions could derive either from an IgE-dependent mechanism (anaphylaxis in the classic sense), or from activation of complement. In many patients, it leads to the formation of specific antibodies. Asparaginase causes the appearance of specific circulating IgGs which have neutralizing properties which are manifested by an increase in the clearance of the enzyme and a reduction in its therapeutic efficacy (Müller HJ, Boos J., Crit. Rev Oncol/hematol 1998; (28): 97-113). These antibodies have been observed with the three forms of asparaginase (E. coli, Erwinia and PEG-asparaginase), although the PEG form seems to be the least immunogenic.

The symptoms are most commonly a simple localized erythema or even simply pain at the injection site, up to laryngeal oedema, bronchospasm and/or hypotension, and, exceptionally, generalized anaphylactic shock in the most serious cases (Zubrod C G, Pediatrics, 1970; (45): 555-9).

The incidence of immuno-allergic reactions due to asparaginase is not clear: between 5 and 70% of the patients treated. On average, a quarter of children develop a severe reaction (Mathé G, Amiel J L, Clarysse A, Recent Results Cancer Res. 1970 (33): 279-87; Woo M H et al., Leukemia, 1998 October; 12(10): 1527-33; Woo M H, Hak L J, Storm M C, Sandlund J T, Ribeiro R C, Rivera G K, J Clin Oncol, 2000 April; 18 (7): 1525-32). Various factors can explain this variability: preparations of asparaginase from different bacterial strains, use of concomitant therapies or administration route (IV or IM). The frequency of the reactions increases with the number of injections in one cycle of treatment and the interval between two courses of treatment (Mathé 1970).

The development of specific antibodies or of hyper-sensitivity reactions is a common cause of interruption of the treatment (Woo M H, Hak L J, Storm M C, Sandlund J T, Ribeiro R C, Rivera G K, J Clin Oncol, 2000 April; 18(7): 1525-32). In patients who have developed specific antibodies, a reduction in the therapeutic efficacy of asparaginase, manifested by a decrease in the duration and/or the incidence of remissions and changes in the pharmacokinetics of the asparaginase are observed. In patients who have exhibited a hyper-sensitivity reaction, the fear of a more severe reaction leads to interruption of the treatment as a precaution. By reason of the premature stoppage of the treatment following allergic reactions, the therapeutic purpose of the asparaginase, which is to achieve a depletion of plasma asparagine for a defined period, is very often not attained.

The pancreas is one of the target organs for the toxicity of asparaginase, probably because of a high level of protein synthesis. This toxicity can take the form either of acute pancreatitis (most commonly) or diabetes.

The mechanism of the acute pancreatitis, whose clinical symptoms range from the benign, spontaneously resolving illness, to complications (haemorrhage, pseudo-cyst), to the fatal, fulminating illness, is poorly understood.

Toxic pancreatitis induced by chemotherapies used in oncology is not uncommon. That due to asparaginase is well documented and many cases have been reported in the literature. The overall incidence due to asparaginase in terms of pancreatitis, for all forms combined, including the PEG forms, varies from 2 to 16% depending on the study (Knoderer H M et al., Pediatr Blood Cancer, 25 Aug. 2006; Müller 1998, 2: 97-113; Alvarez O A et al., Med. Pediatr. Oncol. 2000, 34(3): 200-5). This pancreatitis can be complicated by haemorrhages and pseudo-cysts, but fatalities remain rare. The onset of pancreatitis necessitates the discontinuation of the asparaginase and the initiation of treatment of the pancreatitis. In the light of the studies overall, the administration of repeated and relatively high doses of asparaginase (3000 IU to 60,000 $IU/m^2$/dose) is a predisposing factor.

The other possible pancreatic complication of treatment with asparaginase is the onset of diabetes in 1 to 14% of cases, depending on the study. The mechanism seems to be the decrease in the production of insulin by the β cells of the islets of Langerhans. Hyperglycaemia and glycosuria with no ketosis are the most common symptoms. This effect is reversible and disappears on discontinuation of the treatment. The hyperglycaemia may be increased by concomitant administration with prednisone, but the risk of its occurrence is lower.

Thus, in the case of the treatment of pancreatic cancer the use of asparaginase in patients whose pancreas is damaged could be dangerous and these undesirable effects must be taken into consideration.

The clinical trial in man with the natural form of asparaginase reported above (Lessner et al., 1980) showed that these fears are perfectly justified. On the other hand, the pegylated forms have not yet shown that they were suitable for human clinical use for the treatment of cancer of the pancreas. The results obtained up to the present are limited to in vitro and in vivo results on mouse pancreatic tumour xenograft models. Now, the suitability of the pegylated forms for use in the clinical is far from being established in view of the fact that the molecule is on the one hand still allergenic (Müller et al., 1998) and on the other hand toxic to the pancreas (Knoderer 2006; Müller 1998; Alvarez 2000). Moreover, the clinical trial carried out by Enzon Pharmaceuticals, reported above, regarding the use of Oncaspar® for the treatment of solid tumor has been suspended since toxicity was reached before efficacy (Cowen and Company, "Quick Take: Solide Q4 Results, But Oncaspar Solid Tumor Trial Hits A Snag", Specialty Pharmaceuticals, Feb. 14, 2008).

The encapsulation of asparaginase in erythrocytes in order to improve its therapeutic index has been the subject of development studies. A tolerance study on asparaginase encapsulated in red corpuscles was under-taken by Kravtzoff et al. (C. Eur J Clin Pharmacol, 1996; 51(3-4): 221-5). Thirteen patients mostly suffering from non-Hodgkin lymphomas were given an injection of asparaginase encapsulated in red corpuscles (30 to 200 IU/kg). The study demonstrates an absence of allergic reaction compared to the direct injection of asparaginase (27%). In addition, the injection of asparaginase encapsulated in erythrocytes enables an asparagine depletion lasting for 50 consecutive days.

On the other hand, different studies (WO-A-2006/016247; Millan C G et al., Journal of Controlled Release, 2004, 95(1): 27-49; Kravtzoff R et al., Journal of Pharmacy and Pharmacology, 1990, 42(7):473-476) describe the encapsulation of asparaginase in red corpuscles and the improvement of the pharmacokinetic properties of the encapsulated enzyme in the context of an application for lymphoma and acute lymphoblastic leukaemia.

While the encapsulated form of asparaginase shows the absence of allergic reaction, its administration encapsulated in red corpuscles leaves a certain doubt as to the consequences at the pancreatic level, in particular in patients in a poor general condition or having advanced pancreatic cancer, in the sense that the red corpuscles end up being destroyed and liberate their contents into the vascular compartment. Likewise, its clinical efficacy has not been demonstrated.

The inventors have for the first time demonstrated the efficacy of asparaginase encapsulated in red corpuscles in the mouse pancreatic tumour xenograft model. At the same time, they have obtained results demonstrating the absence of free residual asparaginase in the vascular compartment. They have also demonstrated that the improvement in the pharmacokinetics linked with the use of the red corpuscles makes it possible to use much reduced quantities of enzyme compared to what it would be necessary to use in the free form or in the PEG form, still further reducing the pancreatic toxicity risks. The results obtained by the inventors open the way to the use of encapsulated asparaginase in the treatment of cancer of the pancreas, including patients having an advanced form of this cancer or sensitive patients.

A first object of the invention is thus a suspension of red corpuscles encapsulating asparaginase as a medicament for treating pancreatic cancer.

A second object of the invention is a therapeutic composition or a medicament intended for the treatment of pancreatic cancer, comprising an effective quantity of a suspension of red corpuscles encapsulating asparaginase.

Typically, the red corpuscles are in suspension in a pharmaceutically acceptable saline solution. This can be a standard medium for red corpuscles, in particular a solution of NaCl (preferably 0.9%) possibly with added ingredients such as glucose, dextrose, adenine and/or mannitol. Standard media that can be used are SAG mannitol and ADsol which are solutions based on adenine, glucose, mannitol and sodium chloride. The solution can further contain a preservative such as L-carnitine. The solution can also contain one or more other active principle(s), in particular chemotherapeutic agent(s) intended for the treatment of cancer of the pancreas, as will be described below, or active principle(s) intended for the treatment of the symptoms or disorders which may accompany pancreatic cancer.

The suspension can be ready for use and have a haematocrit suitable for administration by injection or by perfusion without dilution.

It can also be packaged such that it has to be diluted before administration by injection or by perfusion.

According to the invention, the haematocrit of the suspension ready for use advantageously lies between about 40 and about 70%, preferably between about 45 and about 55%, and better about 50%.

In the form for dilution, the haematocrit can be higher, in particular lying between about 60 and about 90%.

The solution is preferably packaged at a volume of about 10 to about 250 ml. The packaging is preferably in a blood bag of the type suitable for a blood transfusion. The whole of the quantity of encapsulated asparaginase corresponding to the medical prescription is preferably contained in the blood bag.

The quantity of encapsulated asparaginase can in particular lie between about 30 and about 300 IU per ml of suspension of red corpuscles. It preferably lies between about 70 and about 150 IU per ml.

A further object of the invention is the use of red corpuscles encapsulating asparaginase or a suspension of such red corpuscles for the preparation of a medicament intended for the treatment of a pancreatic cancer. This use takes account of the characteristics presented for the suspension and the therapeutic composition or medicament.

The invention relates to the treatment of patients whatever the stage of development of the pancreatic cancer, the histological form taken by the cancer and the likelihood of pancreatitis of greater or lesser severity.

The invention relates in particular to:
 the treatment of a patient having a primary tumour of the pancreas;
 the treatment of a patient with local adenopathy, with or without affected local lymphatic ganglia;
 the treatment of a patient having a pancreatic cancer with remote metastases;
 the treatment of a patient having cancer of the head of the pancreas;
 the treatment of a patient having a pancreatic cancer with ductal adenocarcinoma;
 the treatment of a patient having a pancreatic cancer with mucinous cystadenocarcinoma;
 the treatment of a patient having a pancreatic cancer with mucinous intraductal carcinoma;
 the treatment of a patient having a pancreatic carcinoma with acinar adenocarcinoma;
 the treatment of a patient having a pancreatic cancer with cystic tumours, and possibly cystadeno-carcinoma;
 the treatment of a patient having a pancreatic cancer with tumour of the excretory canals of the pancreas;
 the treatment of a patient having a cancer of the endocrine pancreas;
 the treatment of a patient after partial or total resection of the pancreas.

In a further embodiment the invention relates to the increase of the patient survival.

A still further object of the invention is a method for the treatment of pancreatic cancer, in which an effective dose of a suspension of red corpuscles encapsulating asparaginase or of a therapeutic composition or medicament according to the invention is administered to a patient requiring it.

This method can be applied to the different forms of the disease, as was described above.

Administration is effected by intravenous or intra-arterial injection and preferably by perfusion from a blood bag or the like. Administration is typically effected intravenously into the arm or via a central catheter.

In particular, from about 10 to about 250 ml of suspension (one dose), therapeutic composition or medicament according to the invention is administered. Beyond 20 ml, use of perfusion is preferred.

The quantity of encapsulated asparaginase can in particular lie between about 30 and about 300 IU per ml of red corpuscle suspension. It preferably lies between about 70 and about 150 IU per ml.

A treatment comprises the administration of one dose or of several doses according to the protocol decided.

This can provide for several administrations at monthly, fortnightly or weekly intervals, over the recommended duration of the treatment.

This treatment can consist in the administration of the equivalent of 20 to 500 IU of asparaginase per kg of body weight each time (each dose). Preferably, from 50 to 150 IU per kg per dose is administered.

The present invention also provides for combinations of red corpuscles encapsulating asparaginase with standard chemotherapeutic products for the treatment of cancer of the pancreas. Thus the combination can be effected with gemcitabine, cisplatin, oxaliplatin, or 5-fluorouracil in combination with a platinum derivative, for example cisplatin or oxaliplatin. In a first mode, the combination is effected within the suspension, therapeutic composition or medicament according to the invention. According to a second mode, the combination is a combination by separate, concomitant or staggered administration to the same patient.

Asparaginase itself is designated by the CAS number: 9015-68-3. Its usual name is asparaginase; other common names for it are: colaspase, L-asparaginase and L-asparagine aminohydrolase.

The term asparaginase in the sense of the present invention covers asparaginase of any origin, it can in particular be of natural or recombinant origin, and any derivative incorporating asparaginase, such as for example a PEG form, or a fragment retaining the activity of L-asparaginase. It also covers asparaginase whatever its bacterial origin. Thus, the asparaginase may be of the *E. coli* type, in particular *E. coli* HAP-A-1-3, of the *Erwinia chrysanthemi* type or of the *Wolinella succinogenes* type. "Type" is understood to mean that it can be obtained from a culture of the bacterium in question or that it can be recombinant, in other words a form of asparaginase of that bacterium obtained by genetic engineering. In a preferred implementation mode, it is of the *E. coli* HAP-A-1-3 type.

The term asparaginase also covers asparaginase-like substances which in the sense of the invention are bacterial enzymes having an L-asparagine aminohydrolase activity. By way of example, *Acinetobacter* glutaminase asparaginase (AGA) may be cited.

The techniques enabling the encapsulation of active principles in red corpuscles are known and the basic technique by lysis-resealing, which is preferred here, is described in the patents EP-A-101 341 and EP-A-679 101, to which the person skilled in the art will be able to refer. According to this technique, the primary compartment of a dialysis unit (for example dialysis bag or dialysis cartridge) is continuously fed with a suspension of red corpuscles, whereas the secondary compartment contains an aqueous solution hypotonic relative to the suspension of red corpuscles in order to lyse the red corpuscles; next, in a resealing unit, the resealing of the red corpuscles is induced in the presence of asparaginase by increasing the osmotic and/or oncotic pressure, and then a suspension of red corpuscles containing asparaginase is collected.

Among the variations described up to the present, the method described in WO-A-2006/016247, which makes it possible to encapsulate asparaginase in an efficient, reproducible, reliable and stable manner, is preferred. This method comprises the following stages:

1—suspension of a corpuscle pellet in an isotonic solution at a haematocrit level greater than or equal to 65%, refrigeration between +1 and +8° C., 2—measurement of the osmotic fragility using a sample of red corpuscles from this same corpuscle pellet, it being possible to perform stages 1 and 2 in any order (including in parallel), 3—procedure of lysis and internalization of the asparaginase, within a same enclosure, at a temperature constantly maintained between +1 and +8° C., comprising the passage of the suspension of red corpuscles at a haematocrit level greater than or equal to 65% and of a hypotonic lysis solution refrigerated to between +1 and +8° C. in a dialysis cartridge, the lysis parameters being adjusted on the basis of the previously measured osmotic fragility; and 4—a resealing procedure carried out in a second enclosure in the interior of which the temperature lies between +30 and +40° C., and in the presence of a hypertonic solution.

"Internalization" is understood to mean penetration of the asparaginase into the interior of the red corpuscles.

In particular, for the dialysis, the corpuscle pellet is suspended in an isotonic solution at a high haematocrit level, greater than or equal to 65%, and preferably greater than or equal to 70%, and this suspension is refrigerated to between +1 and +8° C., preferably between +2 and +6° C., typically around +4° C. According to a particular mode, the haematocrit level lies between 65 and 80%, preferably between 70 and 80%.

The osmotic fragility is advantageously measured on the red corpuscles just before the lysis stage, in the presence or absence of asparaginase in the suspension. The red corpuscles or the suspension containing them are advantageously at a temperature close to or identical to the temperature selected for the lysis. According to another advantageous characteristic of the invention, the measurement of osmotic fragility carried out is rapidly utilized, in other words the lysis procedure is carried out shortly after the sample is taken. Preferably, this time lapse between sampling and start of lysis is less than or equal to 30 minutes, better still less than or equal to 25 and even to 20 minutes.

For more details concerning the manner of operating the lysis-resealing procedure, with measurement and allowance for the osmotic fragility, the person skilled in the art will be able to refer to WO-A-2006/016247.

The present invention will now be described in more detail by means of implementation modes taken as non-limiting examples.

FIGS. 1 and 2 are graph illustrating the calculation methods of the half-life of Asparaginase or encapsulated Asparaginase.

EXAMPLE 1

Figure 3:
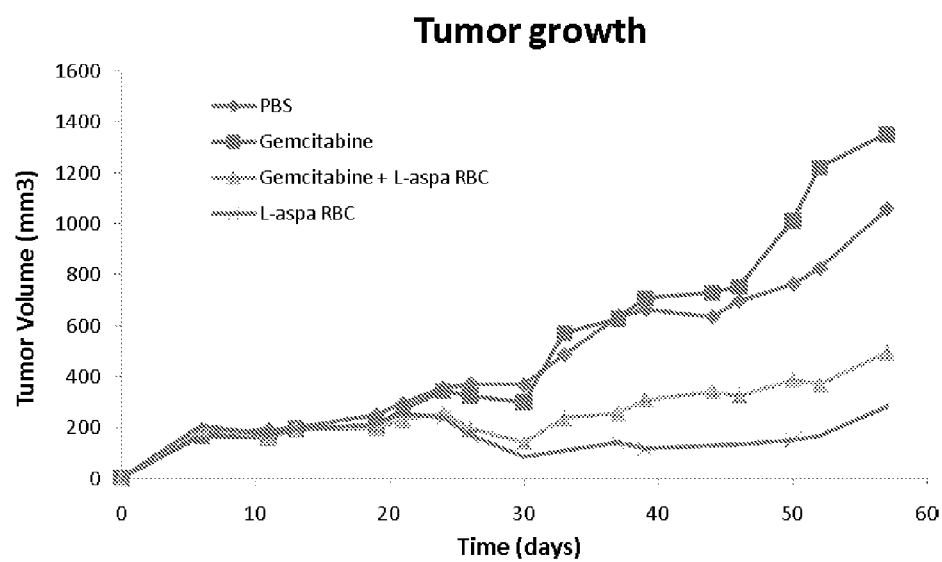
FIG. 3 is a graph illustrating tumour growth inhibition as a function of time in mice treated according to various protocols.

Method for Encapsulation of L-Asparaginase in Murine Red Corpuscles

The L-asparaginase (Kidrolase®, OPI-EUSA Limonest France) is encapsulated in murine red corpuscles (OF1 mice) by the method of hypotonic dialysis in a dialysis bag. The blood is centrifuged beforehand to remove the plasma, and then washed three times with 0.9% NaCl. The haematocrit is adjusted to 70% in the presence of the asparaginase, added to a final concentration of 400 IU/ml of red corpuscles or red blood cells (RBC) before starting the dialysis. The dialysis lasts 50 minutes at 4° C. against a lysis buffer of low osmolarity. The murine red corpuscles are then resealed through the addition of a high osmolarity solution and incubating 30 minutes at 37° C. After two washings with 0.9% NaCl and one washing with Sag-mannitol supplemented with bovine serum albumin BSA (6%), the red corpuscles are adjusted to haematocrit 50%. The red corpuscles encapsulating the L-asparaginase are called L-Aspa RBC. The encapsulation generates L-Aspa RBC at a concentration of 40 IU of asparaginase/ml of RC at 50% haematocrit.

During the encapsulation procedure, the whole blood, the washed RBC, the RBC mixed with the L-asparaginase (before dialysis) and the RBC loaded with L-asparaginase (after dialysis) are tested for:
  haematocrit (Ht)
  average corpuscular volume (ACV)
  average corpuscular haemoglobin concentration (ACHC)
  total haemoglobin concentration and
  cell count.

Aliquots of the cell suspensions are withdrawn before and after the hypotonic dialysis for measurement of the L-asparaginase enzyme activity. The estimation of the L-asparaginase was performed according to the protocol published in: Orsonneau et al., "Dosage automatique en cinétique de l'activité L-Asparaginase plasmatique en suivi thérapeutique des leucémies aigües lymphoblastiques", Ann Biol Clin, 62: 568-572.

EXAMPLE 2

Determination of the Pharmacokinetic and Pharmacodynamic Parameters of L-Aspa RBC in the Mouse Murine L-Aspa RBC were injected into OF1 mice so as to determine the half-life of the L-Aspa RBC in circulation in the mouse and to demonstrate the depletion of L-asparagine in mouse plasma. A single dose of 200 IU/kg was injected into each mouse by the intravenous route.

The half-life of the L-Aspa RBC is 12.39±0.74 days (calculation based on the activity of the enzyme). When the half-life of the murine L-Aspa RBC is calculated via cell labelling (CFSE-L-Aspa RBC), the value is 16.52±3.13 days, and 15.83±3.31 days for RBC simply labelled with CFDA-SE (CFSE RBC).

The depletion of plasma L-asparagine is total (<2 μM), and is obtained 15 minutes after injection of the L-Aspa RBC and persists for at least 20 days.

TABLE 1

Pharmacokinetic data obtained for L-Aspa RBC and for murine RBC labelled with CFDA-SE (CFSE RBC)

| | RBC | | L-asparaginase | |
|---|---|---|---|---|
| | survival at 24 hrs (%) | half-life (days) | survival at 24 hrs (%) | half-life (days) |
| L-Aspa RBC | — | — | 57.9 ± 2.5 | 12.39 ± 0.74 |
| CFSE-L-Aspa RBC | 80.7 ± 0.7 | 16.52 ± 3.13 | 76.7 ± 1.4 | 12.20 ± 1.38 |
| CFSE RBC | 92.7 ± 2.6 | 15.83 ± 3.31 | — | — |

The half-life was calculated as follow:
The intercept point obtained from the plot equation is divided by two. Then the corresponding value of the abscissa is calculated tanks to the plot.

An example of the calculation is shown on FIG. 1, wherein the calculated intercept point is 2,8461.
Half of the intercept point: 1.42
Calculation of the corresponding value of the abscissa: 1.42=(−0.1145*X)+2.8
X=(1.42-2.8)/−0.1145=−1.38/−0.1145=12 days.

More real half-time could be calculated with a second method wherein the ordinate sale is a logarithm scale and the abscissa scale is a linear scale as shown on FIG. 2.
The half-time is calculated as follow:

$$Ln(2)/\text{plot coefficient of the curve.}$$

In the example of FIG. 2 (which is the same example as in FIG. 1) the half-time is:

$$Ln(2)/0.083 = 8.3 \text{ days.}$$

TABLE 2

Measurement of residual L-asparaginase activity as a function of time for L-Aspa RBC and free L-asparaginase

| | Time | | | | | |
|---|---|---|---|---|---|---|
| | 15 min | 24 hr | 3 d | 9 d | 14 d | 20 d |
| L-Aspa RBC | 100 | 57.1 | 46.9 | 39.8 | 24.9 | 10.6 | residual asparaginase activity (%) |
| Free L-Aspa | 100 | 3.3 | 0 | 0 | 0 | 0 |

Furthermore, estimation of the circulating plasma L-asparaginase shows that beyond 24 hours after the injection of the L-Aspa RBC into mice, the values obtained are at the assay detection limit (between 1 and 3 IU/litre).

EXAMPLE 3

Growth Inhibition of Human Pancreatic Tumours in Response to an Injection of L-Aspa RBC in the Mouse The purpose of this experiment is to inject L-Aspa RBC into mice bearing human pancreatic tumours and to observe a tumour growth inhibition. A cell line sensitive to L-asparaginase in vitro, and deficient in L-asparagine synthase, was selected: Mia PaCa-2.

To study the tumour growth inhibition after the injection of L-Aspa RBC, an in vivo protocol was set up with 4 groups of 12 mice. A reference treatment for cancer of the pancreas, gemcitabine, is included in the protocol.

Preparation of Test Substances and Controls

Test substance 1: L-asparaginase loaded into murine red corpuscles (called L-Aspa RBC). The procedure for the preparation of the L-Aspa RBC is described above (see Example 1).
Test substance 2: Gemcitabine
Control substance 2: PBS (gemcitabine uptake buffer)

Culturing of the Mia PaCa-2 Cells

Human pancreatic tumour cells (Mia PaCa-2) in exponential growth phase (origin ATCC: American Type Culture Collection) were subjected to tryptic digestion, then counted and washed before finally being resuspended in a DMEM serum-free medium in order for them to be injected subcutaneously into 48 athymic nude/nude mice.

Animals

The 48 athymic nude/nude (nude balb/c) mice, aged 5-6 weeks and between 18 and 22 g in weight, were supplied by Harlan (France). The animals were kept for 7 days in a specialized SPF (specific-pathogen-free) unit before the treatment.

The 48 mice were divided randomly into 4 groups of 12 mice.

When the tumour volume reached 200 mm³, the mice were subjected to injections of:
- single injection of L-Aspa RBC (200 IU/kg) by the intravenous route in a volume not to exceed 10 ml/kg
- four injections of gemcitabine (60 mg/kg) by the intravenous route.

Planning of Treatments

The planning was organized as follows:
Group 1: the mice were given PBS
Group 2: the mice were given 4 injections of gemcitabine (60 mg/kg), 2 injections per week for 2 weeks
Group 3: the mice were given a single injection of L-Aspa RBC and 4 injections of gemcitabine (60 mg/kg), 2 injections per week for 2 weeks
Group 4: the mice were given a single injection of L-Aspa RBC.

The injection of the different products was effected blind.

Measurement of the tumours was effected regularly (every 3 to 4 days) for 57 days.

Results

FIG. 3 is a graph showing the tumour growth inhibition in the different groups as a function of time.

The two control groups (1 and 2) show regular tumour growth from 0 to 1058±939 mm³ and 1353±1016 mm³ respectively. Group 2 (gemcitabine) does not demonstrate an effect of the medicament on the growth of the pancreatic tumours in the mouse (injection at a tumour volume of 196±57 mm³ and, at 57 days, 1353±1016 mm³). In contrast, the injections of L-Aspa RBC in combination with gemcitabine considerably retard the tumour growth: this treatment was injected when the tumours were 190±43 mm³ and after 57 days the tumour volume is 494±719 mm³ compared to 1353±1016 mm³ for the mice in group 2 treated only with gemcitabine. Finally, the L-Aspa RBC (group 4) are still more effective for tumour growth inhibition than in combination with gemcitabine since after injection at a tumour volume of 193±46 mm³ this reaches only 285±225 mm³ after 57 days.

The murine red corpuscles encapsulating L-asparaginase (L-Aspa RBC) were the most effective treatment in retarding the growth of the human pancreatic tumours implanted in the mouse. Surprisingly, the L-Aspa RBC alone are more effective for tumour growth inhibition than in combination with gemcitabine.

EXAMPLE 4

In Vivo Anti-Tumoral Study of L-Asparaginase Encapsulated in Red Blood Cell in Mice Bearing Pancreatic Tumor PANC-1

The objective of this study was to assess the antitumoral effects of L-asparaginase encapsulated in red blood cells (L-aspa RBC) administered in a human pancreatic tumor (PANC-1) xenograft model.

PANC-1 is a human pancreatic cell line, in vitro sensitive to L-asparaginase. In this study, 4 groups of 15 mice received either L-asparaginase encapsulated in red blood cells, gemcitabine (reference treatment in pancreatic cancer), a combination of both agents or control item. A last group of 10 mice received no treatment and was used as control group.

Preparation of the Test and Control Items

Test item 1: L-asparaginase encapsulated into murine red blood cells (L-aspa RBC). Manufacture procedure of L-aspa RBC was conducted as described in example 1.

Test item 2: gemcitabine (Gemzar®, Eli Lilly and Company)

Control item: PBS (saline solution)

Panc-1 Cell Line Culture

A Log-growing culture of human pancreatic tumor cells, PANC-1 (obtained from ECCAC, UK), was subcloned and the clone no. 6sC was selected based on its growth capacity and sensitivity to asparaginase.

Clone no 6sC was trypsinized, counted, washed and resuspended in serum-free DMEM medium for sub-cutaneous injection to 100 nu/nu athymic mice.

Animals

Hundred athymic Nude mice of 5 week-old, weighing 20 g+/−3 g were supplied by Harlan France. The animals underwent an acclimatization period of 12 days and were maintained in SPF (specific pathogen-free) conditions and continuously controlled conditions of temperature, humidity, photoperiod and air exchange.

Four days after cell implantation, tumor volumes were measured and ranked according to size and median was calculated. Thirty five mice with a tumor volume above the median and 35 mice with a tumor volume below the median were included in the study (70 mice in total).

These animals were randomly assigned into 4 groups of 15 mice and 1 group of 10 mice following a pre-established randomization table. Mice received:
- a single i.v. injection of L-aspa RBC (200 IU/kg). The volume of administration were not greater than 8 ml/kg or one tenth of the animal's blood volume.
- 4 i.v. injections of gemcitabine (80 mg/kg)
- 4 i.v. injections of PBS Treatment Schedule Group 1: mice received 4 injections of PBS every 3 days
Group 2: mice received 4 injections of gemcitabine every 3 days
Group 3: mice received a single injection of L-aspa RBC and 4 injections of gemcitabine every 3 days
Group 4: mice received a single injection of L-aspa RBC
Group 5: no treatment Tumor measurements were recorded 3 times a week (on Mondays, Wednesday and Friday) during 43 days.

Results

Figure 4:
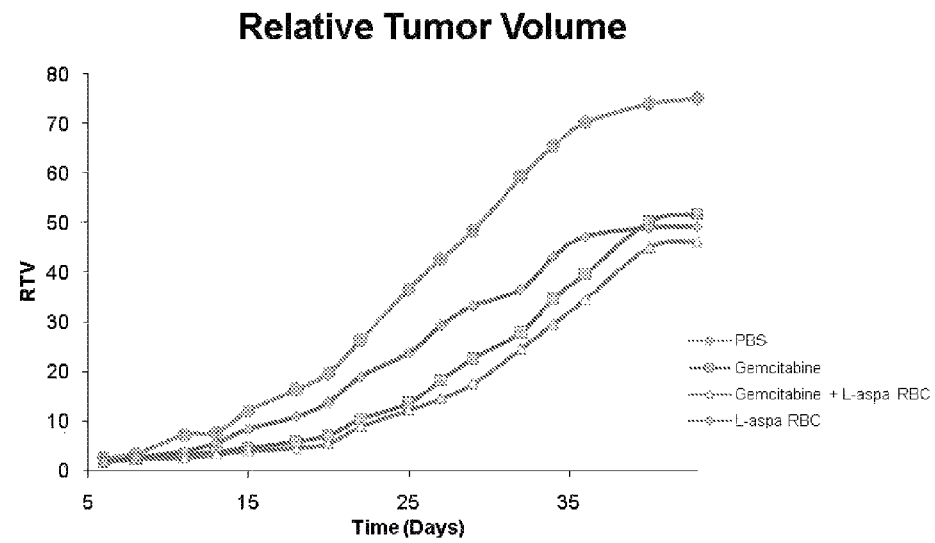
FIG. 4 illustrates relative tumor volume versus time for each group of mice in a xenograft model.

FIG. 4 illustrates relative tumor volume versus time for each group. The relative tumor volume is calculated by dividing the tumor volume at a given day by the tumor volume before treatment avoiding the bias due to statistical difference in tumor volume between groups on the day of injection.

FIG. 4 shows that the relative tumor volume in the gemcitabine and L-aspa RBC combined with gemcitabine groups increased more slowly than in the PBS group (51.8±17.1; 46.3±29.7 and 75.1±31.0 at day 43 respectively). It is noteworthy that the combination treatment tends to be more effective on tumor growth inhibition than gemcitabine alone.

This representation highlights the efficacy of a single injection of L-aspa RBC as the relative tumor volume was found to increase more slowly than in the control group (49.3±32.2 versus 75.1±31.0 at day 43).

Figure 5:
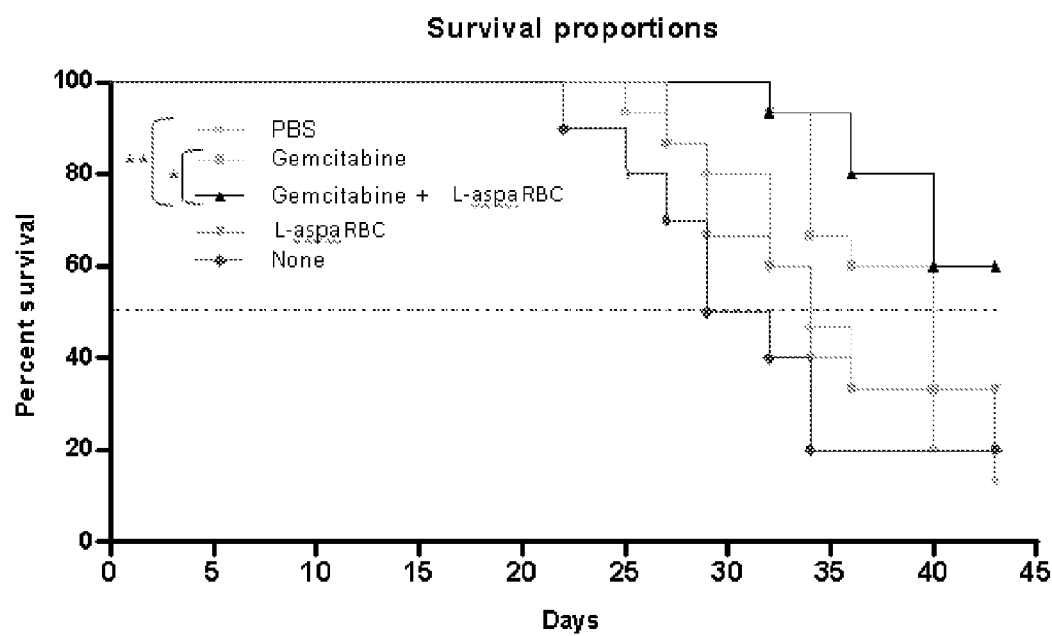
FIG. 5 is a graphic representation of mouse survival for each treatment group of mice in a xenograft model.

FIG. 5 is a graphic representation of mouse survival for each treatment group. Treatment with L-aspa RBC or gemcitabine alone were not better than PBS as the graphs nearly overlap entirely (only 20% of mice remained in the gemcitabine group, 33% for mouse of L-aspa RBC group and 13% percent of the mice remained in the PBS group at day 43). Differences between groups were not statistically significant. However, mouse survival was greatly improved by the combination of gemcitabine with L-aspa RBC (60% of mice still alive at day 43) and the difference was found to be significant ($p<0.01$). Moreover, gemcitabine combined with L-aspa RBC compared to gemcitabine alone gave a statistically significant improvement in mouse survival ($p<0.05$).

These results indicate that a single i.v. injection of L-aspa RBC inhibited tumor growth in mice bearing human pancreatic cell line, and that gemcitabine treatment is enhanced by the presence of L-aspa RBC. This statement is supported by the best inhibition of tumor growth observed compared to the other groups and the proportions of surviving animals at the end of the study.

The invention claims is:

1. A method for the treatment of pancreatic cancer, which comprises the administration to a human patient with pancreatic cancer of an effective dose of a suspension of red corpuscles encapsulating asparaginase.

2. The method according to claim 1, wherein the suspension contains between 30 and 300 IU of asparaginase per ml.

3. The method according to claim 1, wherein the suspension contains between 70 and 150 IU of asparaginase per ml.

4. The method according to claim 1, wherein the suspension has a volume of 10 to 250 ml.

5. The method according to claim 1, wherein one administers from 20 to 500 IU of asparaginase per kg body weight and per dose.

6. The method according to claim 1, wherein one administers from 50 to 500 IU of asparaginase per kg body weight and per dose.

7. The method according to claim 1, which comprises the administration to a patient in need thereof of an effective dose of a suspension of red corpuscles encapsulating asparaginase and of a chemotherapeutic agent.

8. The method according to claim 7, wherein the chemotherapeutic agent is selected from the group consisting of gemcitabine, cisplatin, oxaliplatin and combination of 5-fluorouracil with a platinum derivative.

9. The method according to claim 7, wherein the 5-fluorouracil is in combination with a platinum derivative selected from the group consisting of cisplatin and oxaliplatin.

10. The method according to claim 7, wherein the chemotherapeutic agent is formulated in the suspension of red corpuscles.

11. The method according to claim 7, wherein the chemotherapeutic agent and the suspension are administered to the patient by separate, concomitant or staggered administration.

12. The method for according to claim 1, wherein the suspension of red corpuscles encapsulating asparaginase is administered to the patient having a pancreatic cancer, in order to increase patient survival.

* * * * *